US010335827B2

(12) United States Patent
Johnson et al.

(10) Patent No.: US 10,335,827 B2
(45) Date of Patent: *Jul. 2, 2019

(54) ULTRASONIC TRANSDUCER DEVICE WITH THROUGH-SUBSTRATE VIA

(71) Applicant: Texas Instruments Incorporated, Dallas, TX (US)

(72) Inventors: Peter B. Johnson, Sunnyvale, CA (US); Ira Oaktree Wygant, Palo Alto, CA (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 206 days.

This patent is subject to a terminal disclaimer.

(21) Appl. No.: 15/345,741

(22) Filed: Nov. 8, 2016

(65) Prior Publication Data
US 2017/0050217 A1    Feb. 23, 2017

Related U.S. Application Data

(63) Continuation of application No. 13/779,376, filed on Feb. 27, 2013, now Pat. No. 9,520,811.

(51) Int. Cl.
| H02N 1/00 | (2006.01) |
| B06B 1/02 | (2006.01) |
| A61B 8/00 | (2006.01) |

(52) U.S. Cl.
CPC .......... *B06B 1/0292* (2013.01); *A61B 8/4483* (2013.01); *H02N 1/002* (2013.01);
(Continued)

(58) Field of Classification Search
CPC ........ H02N 1/002; H02N 1/006; H02N 1/008; A61B 8/4483; B06B 1/0292; B06B 2201/76
(Continued)

(56) References Cited

U.S. PATENT DOCUMENTS 6,312,581 B1    11/2001 Bruce et al.
7,405,637 B1 *   7/2008 Mehta .................. H01P 1/2056
                                                              333/207
(Continued)

FOREIGN PATENT DOCUMENTS

CN    101223633 A    7/2012
DE    102005058977   6/2007
(Continued)

OTHER PUBLICATIONS

State Intellectual Property Office of PRC Notification of First Office Action, Search Report, dated Apr. 1, 2017.
(Continued)

*Primary Examiner* — John K Kim
(74) *Attorney, Agent, or Firm* — Jacqueline J. Garner; Charles A. Brill; Frank D. Cimino

(57) ABSTRACT

A Capacitive Micromachined Ultrasonic Transducer (CMUT) device includes at least one CMUT cell including a first substrate having a top side including a patterned dielectric layer thereon including a thick and a thin dielectric region. A membrane layer is bonded on the thick dielectric region and over the thin dielectric region to provide a movable membrane over a micro-electro-mechanical system (MEMS) cavity. A through-substrate via (TSV) includes a dielectric liner which extends from a bottom side of the first substrate to a top surface of the membrane layer. A top side metal layer includes a first portion over the TSV, over the movable membrane, and coupling the TSV to the movable membrane. A patterned metal layer is on the bottom side surface of the first substrate including a first patterned layer portion contacting the bottom side of the first substrate lateral to the TSV.

18 Claims, 11 Drawing Sheets

(52) U.S. Cl.
CPC ............. *H02N 1/006* (2013.01); *H02N 1/008* (2013.01); *B06B 2201/76* (2013.01)

(58) Field of Classification Search
USPC .................................................. 310/300, 309
See application file for complete search history.

(56) References Cited

U.S. PATENT DOCUMENTS

| | | | |
|---|---|---|---|
| 7,741,686 B2 | 6/2010 | Khuri-Yakab et al. | |
| 7,799,678 B2* | 9/2010 | Kropewnicki | .... H01L 21/76898 257/E21.586 |
| 7,969,013 B2* | 6/2011 | Chen | ................. H01L 21/76898 257/773 |
| 8,105,941 B2* | 1/2012 | Huang | .............. H01L 21/76898 257/E21.577 |
| 8,143,704 B2* | 3/2012 | West | ..................... H01L 23/481 257/621 |
| 8,304,893 B2 | 11/2012 | West | |
| 8,324,006 B1 | 12/2012 | Adler et al. | |
| 8,563,345 B2* | 10/2013 | Adler | ..................... B06B 1/0292 257/416 |
| 8,859,414 B2 | 10/2014 | West | |
| 9,351,081 B2* | 5/2016 | Johnson | ................ B06B 1/0292 |
| 9,520,811 B2* | 12/2016 | Johnson | ................ B06B 1/0292 |
| 9,937,528 B2* | 4/2018 | Johnson | ................ B06B 1/0292 |
| 2005/0082682 A1 | 4/2005 | Liu | |
| 2007/0299345 A1* | 12/2007 | Adachi | .................... A61B 8/12 600/459 |
| 2008/0194053 A1 | 8/2008 | Huang | |
| 2008/0203556 A1 | 8/2008 | Huang | |
| 2009/0140357 A1 | 6/2009 | Kupnik et al. | |
| 2011/0187000 A1 | 8/2011 | West | |
| 2012/0068302 A1 | 3/2012 | Beierke et al. | |
| 2012/0112324 A1 | 5/2012 | Huang | |
| 2012/0187508 A1 | 7/2012 | Adler et al. | |
| 2014/0187956 A1* | 7/2014 | Rice | ...................... B06B 1/0662 600/459 |
| 2014/0239769 A1* | 8/2014 | Johnson | ................ B06B 1/0292 310/300 |
| 2015/0137285 A1* | 5/2015 | Shim | ...................... B81B 7/007 257/416 |
| 2017/0050217 A1* | 2/2017 | Johnson | ................ B06B 1/0292 |

FOREIGN PATENT DOCUMENTS

| | | |
|---|---|---|
| EP | 1796025 | 11/2006 |
| WO | WO2007036922 | 4/2007 |

OTHER PUBLICATIONS

PCT Notice of Transmittal of the International Search Report and the Written Opinion of the International Searching Authority, or the Declaration dated Jul. 16, 2014.

Xuefeng Zhuang, et al., "Wafer-Bonded 2-D CMUT Arrays Incorporating Through-Wafer Trench-Isolated Interconnects with a Supporting Frame," IEEE Transactions on Ultrasonics, Ferroelectrics and Frequency Control, vol. 56, No. 1, pp. 182-192, Jan. 2009.

"Fabrication of 3D Integrated heterogeneous Systems," IMAPS Nordic, TØnsberg, Norway, Sep. 14-15, 2009.

* cited by examiner

ULTRASONIC TRANSDUCER DEVICE WITH THROUGH-SUBSTRATE VIA

CROSS-REFERENCE TO RELATED APPLICATIONS

Under 35 U.S.C. § 120, this continuation application claims benefits of and priority to U.S. patent application Ser. No. 13/779,376, filed on Feb. 27, 2013, the entirety of which are hereby incorporated herein by reference.

BACKGROUND

Capacitive micromachined ultrasonic transducer (CMUT) devices are becoming increasingly popular in medical applications. For example, CMUT devices have been used to improve medical ultrasound imaging probes. CMUT devices have also been used to provide high-intensity focused ultrasound for use in medical therapy. Conventional CMUT devices are typically produced directly on a silicon substrate (i.e. on a silicon wafer). For instance, conventional CMUT devices are often fabricated using a micro-electro-mechanical system (MEMS) manufacturing technique in which a release layer is etched out, leaving a free-standing (flexible) membrane. The top of the membrane is metalized to provide a top (electrode) plate, and the membrane is then used as a transducer to transmit and receive ultrasonic signals.

Conventional CMUT devices utilize bond pads to provide electrical contact to the top plate for each of the CMUT elements in the device, such as a plurality of bond pads for a CMUT device including a plurality of CMUT elements arranged in a CMUT array. Since the bond wire is elevated above the bond pad, the bond pad is placed remote from the CMUT elements in the CMUT array to facilitate packaging. This constraint not only increases the CMUT device die size due to the need for interconnect routing lines, but it also complicates the packaging process. Both the increased die size and the complicated packaging process increase the cost of packaged CMUT die.

SUMMARY

Disclosed embodiments describe solutions to the CMUT device problems with conventional utilization of bond pads for connection to the top plate of each CMUT cell which is recognized to substantially constrain the design and increase size of CMUT devices including 2 dimensional (2D) CMUT arrays of CMUT elements, and also impair their performance. To connect the bond pads to each CMUT element of a conventional large 2D CMUT array involves extensive use of metal interconnect traces on the top side of the CMUT die, thereby increasing the die size and reducing CMUT performance. For CMUT arrays containing a large number CMUT elements (e.g., >10×10 array of CMUT elements) the use of metal interconnect traces to provide contact to each element generally becomes prohibitively complicated for the internal elements, and alternative connection schemes are needed. One such connection scheme is the use of through-substrate connections.

Disclosed embodiments include CMUT devices having through-substrate vias (TSVs) which allows bottom side device (die) contact to make connections to the top plate (top electrode) of the CMUT cells or CMUT elements including a plurality of CMUT cells through the die to facilitate the production of 2D CMUT arrays. For CMUT devices having a plurality of CMUT elements, the top electrodes are separate for each CMUT element allowing separate addressing of the respective elements using a single TSV for each element, and there is generally a electrically common bottom side electrode (e.g., a solid sheet of Si substrate) for all CMUT elements on the device. In other embodiments the CMUT device can have an electrically common top electrode for all CMUT elements and an individual bottom electrode for each element to allow separate addressing of the respective elements.

BRIEF DESCRIPTION OF THE DRAWINGS

Reference will now be made to the accompanying drawings, which are not necessarily drawn to scale, wherein.

DETAILED DESCRIPTION

Figure 1A:
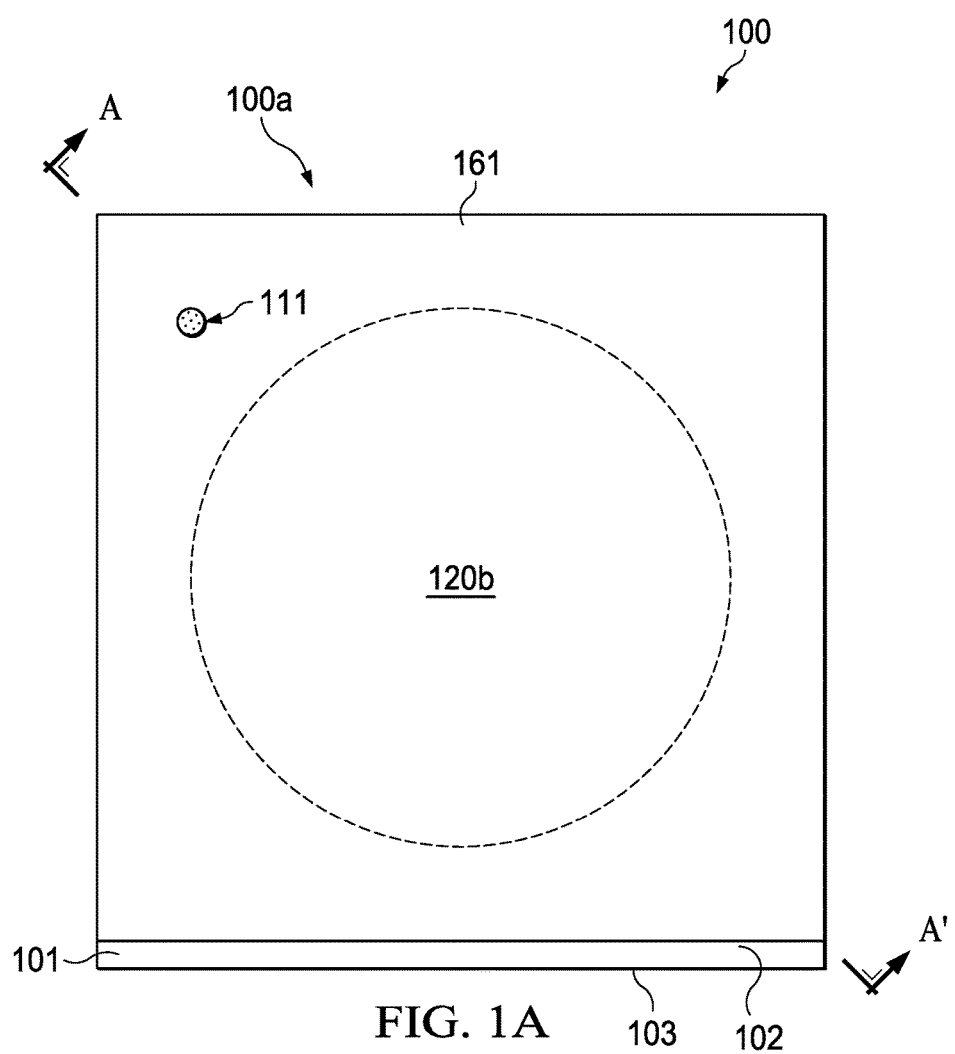
FIG. 1A is a top view depiction an example CMUT device shown as a CMUT element with a single CMUT cell, according to an example embodiment.

Example embodiments are described with reference to the drawings, wherein like reference numerals are used to designate similar or equivalent elements. Illustrated ordering of acts or events should not be considered as limiting, as some acts or events may occur in different order and/or concurrently with other acts or events. Furthermore, some illustrated acts or events may not be required to implement a methodology in accordance with this disclosure.

Regarding nomenclature used herein, the smallest CMUT sensor entity is a CMUT sensor cell. Multiple CMUT sensor cells can be connected in parallel (e.g., with an electrically common movable membrane 120b) to form a CMUT element. A CMUT element can have any number (≥1) of CMUT cells. Typically, the more CMUT cells in an element the greater the ultrasonic output pressure that the element can generate responsive to a given stimulus. A CMUT array (device/die) can have any number of CMUT elements. One of the electrodes (e.g., top) of the respective CMUT elements can be electrically isolated from the other electrodes (e.g., top) of the other CMUT elements to allow each CMUT element to be connected independently to be individually addressable. As described herein, having the movable membranes 120b for each CMUT cell in a CMUT element be electrically common allows addressing of all cells in the CMUT element by a single TSV.

FIG. 1A is a top view depiction an example CMUT device 100 shown as a CMUT element with a single CMUT cell 100a, according to an example embodiment. A cut line A-A' is provided for the cross sectional depiction shown in FIG. 1B and other FIGS. 2A-H described below. The CMUT cell 100a includes a through-substrate via (TSV) 111, and a first substrate 101 of a single crystal material (e.g., bulk single crystal silicon or a silicon epitaxial layer on a single crystal substrate) having a top side 102 and a bottom side 103.

Figure 1B:
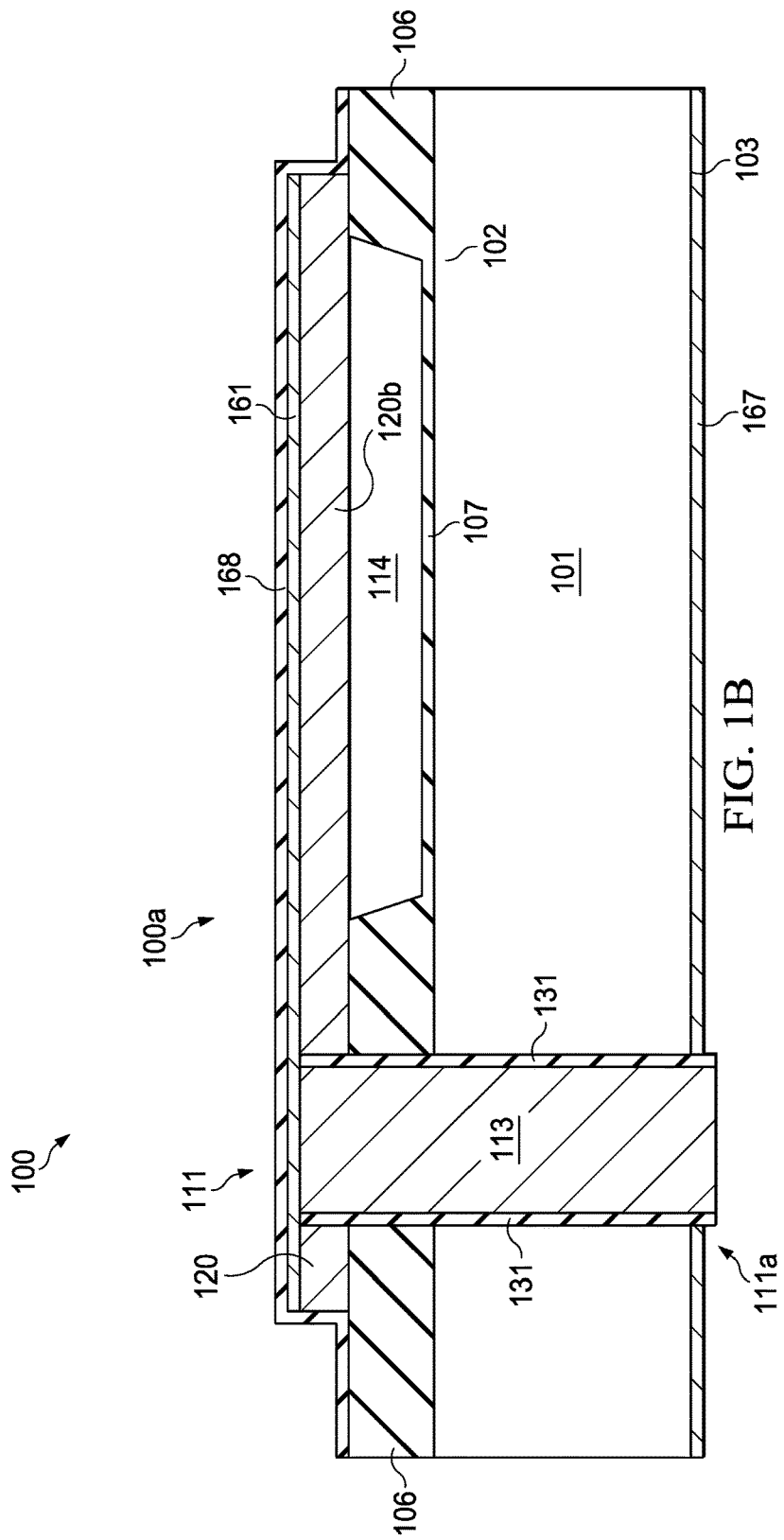
FIG. 1B is cross sectional depiction of the example CMUT device/element/cell shown in FIG. 1A along the cut line A-A' shown.

As shown in FIG. 1B, the top side 102 includes a patterned dielectric layer thereon including a thick dielectric region 106 and a thin dielectric region 107. The TSV 111 extends a full thickness of the first substrate 101 to the top surface of the membrane layer 120. The TSV 111 is electrically isolated from the first substrate 101 and membrane layer 120 by a dielectric liner 131. Although the dielectric liner 131 is shown along the full length of the TSV 111 including on the sidewalls of the thick dielectric region 106, in the case of a thermally formed dielectric liner 131 (e.g., silicon oxide), as opposed to a deposited dielectric liner 131, the dielectric liner 131 will not grow on the sidewalls of the thick dielectric region 106, and thus not be on the sidewalls of the thick dielectric region 106. TSV 111 includes a TSV filler material 113, such as Cu in one particular embodiment. TSV 111 is also shown including optional protruding TSV tips 111a which protrude from the bottom side 103 of the first substrate 101.

The membrane layer 120 of a second substrate shown as a silicon on insulator (SOI) substrate 115 (depicted in FIG. 2A) is bonded to the thick dielectric regions 106 and is over the thin dielectric regions 107 of the first substrate 101 to provide a movable membrane 120b over the MEMS cavity 114 shown. The bonding can comprise vacuum bonding, such as vacuum fusion bonding. A patterned top side metal layer (e.g., an AlCu layer) 161 is over the top of the TSV 111 and over the top of the movable membrane 120b including a metal layer portion coupling the TSV 111 to the movable membrane 120b. A dielectric passivation layer 168 is shown over the top of the CMUT cell 100a.

The first substrate 101 can comprise single crystal silicon, or epitaxial silicon on single crystal silicon. The first substrate 101 typically has a resistivity less than or equal to (≤) 0.1 Ω-cm, and can be doped p-type or n-type. CMUT cell 100a is shown including a patterned metal layer 167 on a bottom side 103 of the first substrate 101 which provides a first electrode contact on a bottom side 103 of the CMUT cell 100a to realize a fixed electrode. As noted above, in the case of a CMUT device including a plurality of CMUT elements each including a plurality of CMUT cells 100a, the fixed electrode contact provided by patterned metal layer 167 is to a common bottom side fixed electrode (e.g., a solid sheet of the first substrate 101, such as a Si sheet) for all CMUT elements on the CMUT device.

TSV 111 provides a bottom side connection to movable membrane 120b which provides a top plate for the CMUT cell 100a of the CMUT device 100. As noted above, for CMUT devices having a plurality of CMUT elements, the top electrodes can be separate for each CMUT element allowing separate addressing of the respective elements using a respective TSV 111 for each element. No top side contact, nor bond pads are thus needed by the CMUT device 100.

It is noted CMUT device thicknesses and dimensions can be adjusted to fit specific applications. For example, typical example dimensions for an airborne ultrasound application at 180 kHz operation is a CMUT cell having a movable membrane 120b 1.12 mm in diameter, a patterned top side metal layer 161 plate width of 1.32 mm (100 μm plate overlap of the top side metal layer 161 on the sides of the CMUT cell 100a), and a movable membrane 120b thickness of 14 μm.

FIGS. 2A-2H are cross-sectional diagrams showing processing progression for an example method of forming CMUT devices during different stages of fabrication, according to an example embodiment. Although the CMUT device is described being formed having a single element with a single CMUT sensor cell, as noted above disclosed CMUT devices may be formed having a plurality of CMUT elements each with one or more CMUT cells to form a CMUT array having a plurality of CMUT elements (see FIG. 3 described below).

The embodiment described as shown in FIGS. 2A-H is thus for illustration only and is one particular embodiment which describes formation of a CMUT device having a single CMUT element with a single CMUT cell 100a. Other techniques for forming disclosed CMUT devices can be used without departing from the scope of this disclosure, including forming CMUT devices including a plurality of disclosed CMUT elements. Several CMUT cells within a CMUT element can be connected in parallel by coupling together movable membranes 120b of CMUT cells in a given CMUT element, such as to increase the output pressure over a given area. Connecting CMUT cells in parallel reduces the impedance (for driving). The CMUT elements can be electrically isolated from one another for use independently to facilitate beam steering or for improved spatial resolution over a large area. One can also drive/sense the CMUT elements differentially to improve common mode signals or mitigate manufacturing asymmetries.

Thick dielectric regions 106, such as comprising a silicon oxide layer, are provided on a top side 102 of a first substrate 101. First substrate 101 can generally comprise any single crystal substrate material, including silicon-based substrates, or other substrates. The first substrate 101 provides a low substrate resistivity of ≤0.1 Ω-cm, such as about 0.01 Ω-cm.

In one particular embodiment, to form thick dielectric regions 106 a thick silicon oxide layer is grown to a thickness of 4.5 μm to 5.5 μm using a high pressure oxidation (HiPOx) process. The use of HiPOx facilitates the rapid growth of thick thermal oxide layers and generally provides good thickness control across the die of typically less than ±1%. One particular example set of HiPOx process conditions include a temperature of 1,000° C. at 25 atmospheres pressure in steam for 9.5 hours on virgin first substrates 101 (e.g., bulk single crystal silicon wafers), and the alignment marks for photolithography are etched later in the process.

As an alternative, thick dielectric regions 106 may also comprise conventional thermally grown silicon oxide (e.g., using a LOCal Oxidation of Silicon (LOCOS) process where silicon dioxide is formed in selected areas (here thick dielectric regions 106) on a silicon wafer generally using a silicon nitride as a mask to oxidation, or be a deposited dielectric layer, including silicon oxide or other dielectric material. However, the LOCOS approach with conventional oxidation will generally not yield 5 μm thick (or thicker) oxide layers, and deposited dielectric (e.g., oxide) films will generally not provide less than ±1% thickness control across the die.

The substrate vendor's laser scribe generally present can be used to ensure a minimum of surface contamination or roughness which will facilitate subsequent wafer bonding steps. Masking and etching of front side alignment marks can follow. Resist strip and a pre-clean process can help ensure a smooth surface for the thick dielectric regions 106 used later in the process for bonding the membrane layer 120 of a SOI substrate 115 or a second substrate such as a standard bulk silicon substrate thereto.

A first masking level "CELLETCH" uses thick photoresist in order to support the subsequent etch through the thick dielectric regions 106 (e.g., thick silicon oxide layer) to initially begin to define at least one etched single cell CMUT element for each CMUT array/die on the first substrate 101 (e.g., a Si wafer). A plasma etch which is non-polymerizing can be used for etching a first portion of the thick dielectric region 106, such as to etch about 4.65 µm of silicon oxide when thick dielectric regions 106 comprise silicon oxide and have a thickness of about 5 µm to 5.3 µm. A sidewall slope of ~80° is generally desirable and can be achieved from the natural resist erosion. The remaining portion of the thick dielectric region 106 (e.g., 0.5 µm silicon oxide) after plasma etch can be removed by wet etch that provides etch selectivity relative to the substrate material (e.g., Si) to avoid damaging the top side 102 of the first substrate 101.

About 50% of the top side 102 of the first substrate 101 (e.g., a wafer) will generally be open (exposed) during the etch of the thick dielectric region 106. The resist is then stripped (e.g., a wet strip process). Following an appropriate pre-oxidation clean, in an oxidation step a thin (e.g., 0.3 µm) CMUT cell oxide can be grown to form thin dielectric regions 107.

Figure 2A:
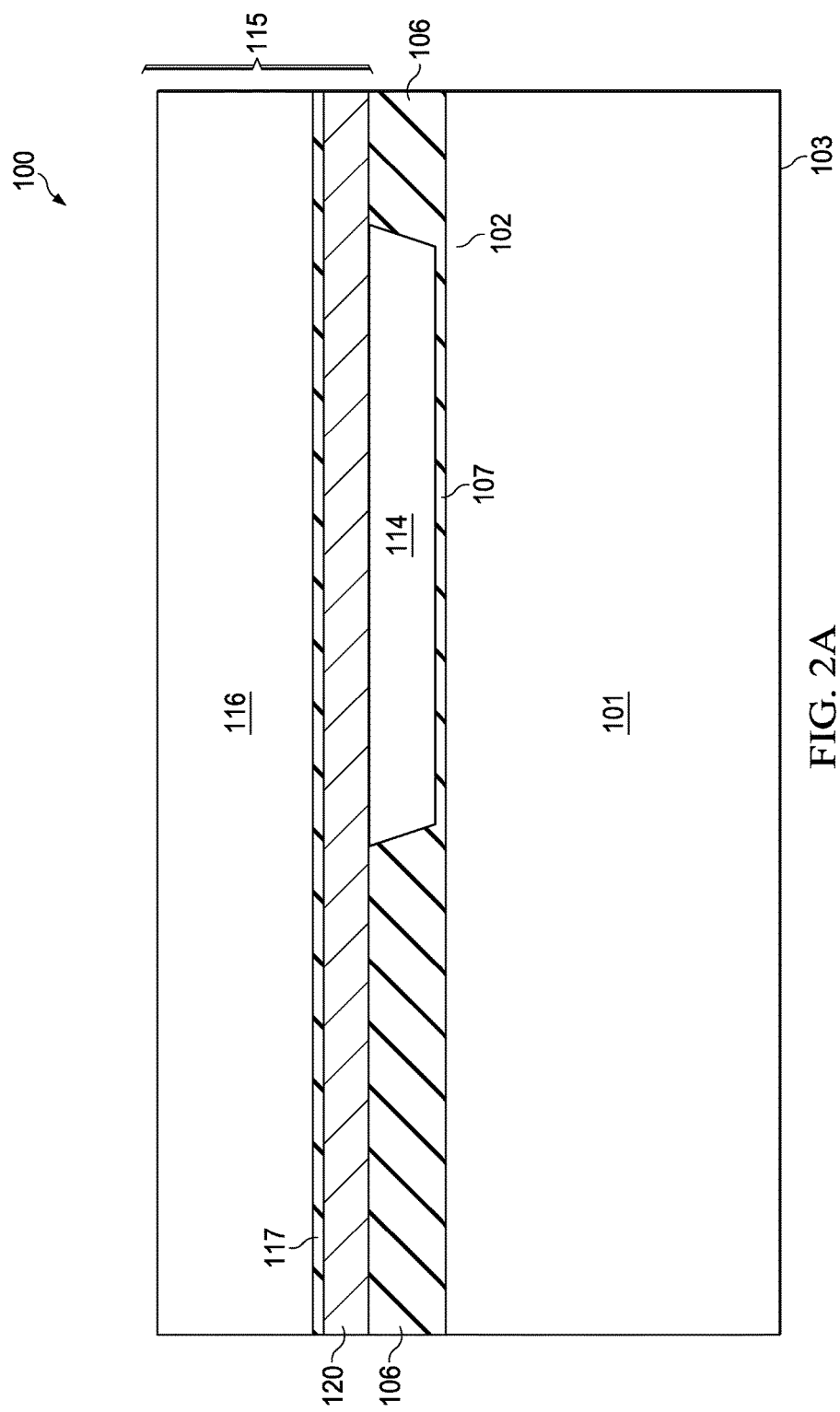
FIGS. 2A-H are cross-sectional diagrams showing processing progression for an example method of forming a CMUT device, according to an example embodiment.

FIG. 2A shows a cross sectional depiction of the CMUT device in-process after vacuum fusion bonding of a SOI substrate (e.g., SOI wafer) 115 comprising a handle (e.g., wafer) 116, buried dielectric layer 117 (generally referred to in the art as a "buried oxide layer" or "(BOX) layer") and membrane layer 120 (e.g., generally referred in the art of SOI as the "active layer"). The membrane layer 120 is bonded to the thick dielectric regions 106 of the first substrate 101.

The handle 116 being sacrificial can represent any suitable semiconductor wafer formed from any suitable material(s), such as undoped or lightly-doped (n or p-doped) silicon. The buried dielectric layer 117 also being sacrificial can be any suitable layer(s) of electrically insulative (dielectric) material(s), such as a silicon oxide layer. The membrane layer 120 represents any suitable layer(s) of substrate material(s), such as doped single crystal silicon. In particular embodiments, the handle 116 comprises a silicon wafer with a resistance of about 5 to 10Ω-cm, the buried dielectric layer 117 represents a silicon oxide layer that is about 1.5 µm to 2.5 µm thick, and the membrane layer 120 represents doped silicon with a resistance of about 5Ω-cm is about 14 µm±5 µm thick. For electrical interconnection purposes between cells or elements, the membrane layer 120 can include a metal layer thereon which renders the pathway provided a low resistivity pathway.

However, as noted above, as an alternative to SOI substrates to reduce cost, a second substrate comprising a standard silicon bulk substrate material (e.g., bulk Si wafer) can be bonded to the thick dielectric regions 106 of the first substrate 101 (CMUT substrate/wafer). In this embodiment, after bonding, the second substrate material can be thinned by backgrinding and polishing to the desired target membrane thickness, such as 14 µm±5 µm thick.

For embodiments where the CMUT device/die includes a plurality of CMUT elements (a CMUT array), the membrane layer 120 can be electrically common for all the CMUT cells in each CMUT element. Each CMUT element can have a separate/unique top plate including a plurality of electrically connected movable membranes 120b for the cells within the elements, which can be electrically connected through a dedicated TSV accessible from the bottom side 103 of the first substrate 101. Low resistivity of the top plate of each CMUT element can be provided by subsequent metal deposition on the movable membrane 120b and patterning process steps as described below. Proper known bonding procedures including cleans and plasma pre-treatments can be used.

For vacuum fusion wafer bonding, as is commonly known in the art, attributes which ensure good wafer bonding include the bonding surfaces being smooth with a surface roughness typically less than 3A. Grown thermal oxide and silicon substrates generally satisfy this requirement. Prior to bonding the surfaces can be treated with an RCA clean (SC-1, where SC stands for Standard Clean), with a 1:1:5 solution of $NH_4OH$ (ammonium hydroxide)+$H_2O_2$ (hydrogen peroxide)+$H_2O$ (water) at 75 or 80° C. typically for 10 minutes. The second RCA clean step is a short immersion in a 1:50 solution of HF+$H_2O$ at 25° C., in order to remove the thin oxide layer and some fraction of ionic contaminants. The third and last step RCA clean (called SC-2) is performed with a 1:1:6 solution of HCl+$H_2O_2$+$H_2O$ at 75 or 80° C. This treatment effectively removes the remaining traces of metallic (ionic) contaminants. A $N_2$ plasma activation and a DI water rinse can follow. The vacuum bonding is typically performed at a pressure less than $8 \times 10^5$ mbar. As a final step the bonded surfaces are annealed in $N_2$ for several hours, such a 4 hour 1050° C. $N_2$ anneal.

The handle 116 is then removed after bonding, such as by backgrinding the handle 116 to about a 150 µm post-backgrind target, performing a second 4 hour 1050° C. anneal after backgrinding prior to a wet etch of the handle remaining after backgrind, and then wet etching the remaining handle. The handle remaining after backgrind when the handle 116 comprises silicon can be etched in a wet silicon etch, such as using a hydroxide (e.g., KOH or TMAH), stopping on the buried dielectric layer 117. Masking and etching the movable membrane (e.g., silicon plate) 120b removes the membrane layer 120 over the alignment marks to reopen the alignment marks and enable proper alignment for subsequent process steps. Since the membrane layer 120 is generally a relatively thick layer for etching (e.g., about 14 µm thick), a Bosch etch can compensate for resist erosion during the etch of the membrane layer 120. As known in the art, the Bosch process, also known as pulsed or time-multiplexed etching, alternates repeatedly between two modes/phases to achieve nearly vertical etched structures.

Figure 2B:
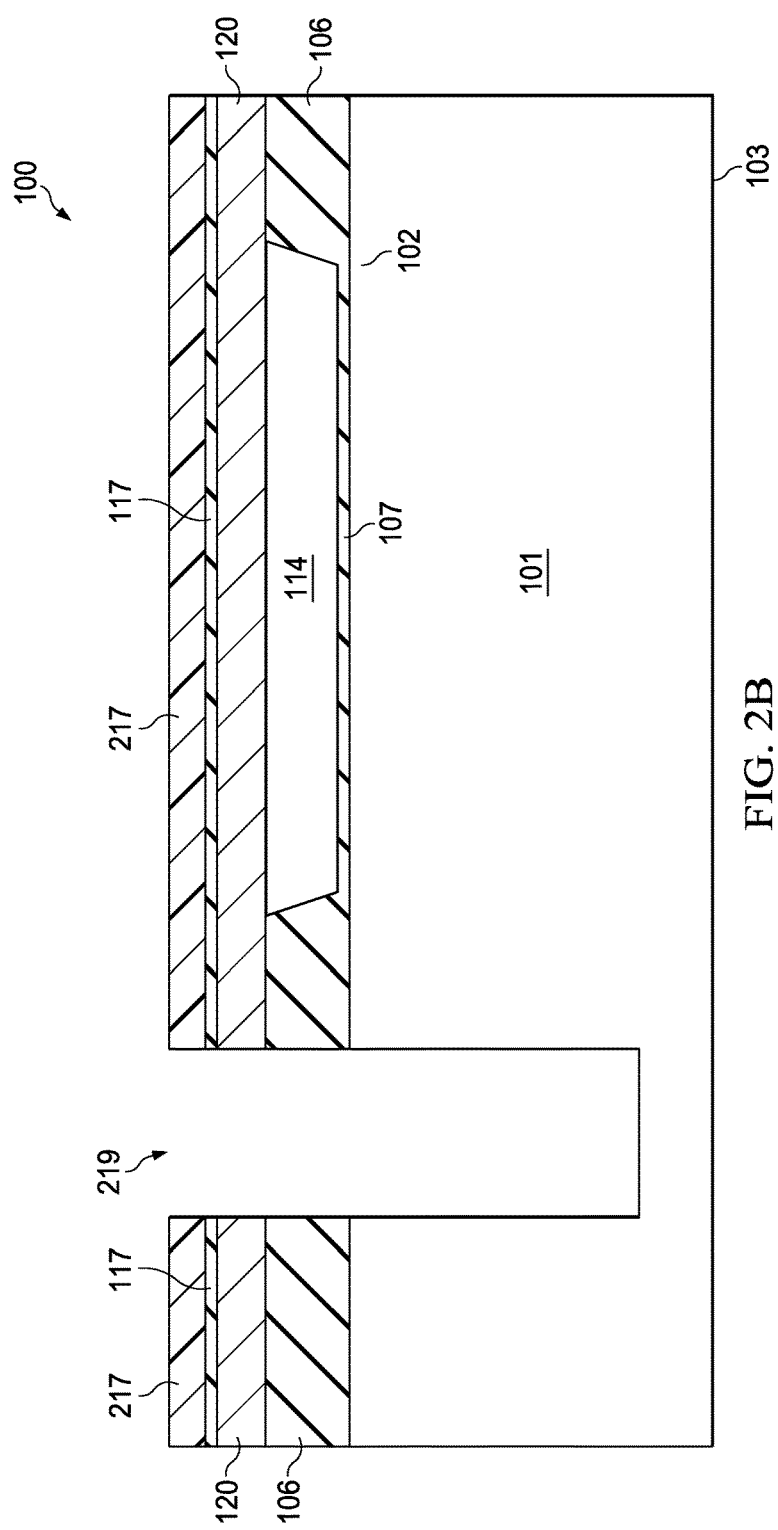

FIG. 2B shows a cross sectional depiction of the CMUT device in-process after the masking level Mask "TSV-HOLE" (Mask #2). The TSV hole (an embedded via) 219 in one particular embodiment is 30 µm in diameter and 150 µm deep (total depth). The resist 217 should be thick enough to support etching through the stack presented, such as a 1.1 µm buried dielectric layer 117, plus a 14 µm membrane layer 120, plus a 5.1 µm thick dielectric region 106, plus 130 µm into the first substrate 101. The TSV hole 219 is then etched. Separate etch tools can be used for etching the buried dielectric layer 117 (e.g. silicon oxide) and Bosch etch for etching the first substrate 101 in the case of silicon.

The resist 217 is then stripped and a dielectric liner 131 (e.g., a 0.5 µm dielectric oxide) is deposited, or is thermally grown on the semiconductor surfaces within the embedded via/TSV hole 219. A diffusion barrier metal layer formed on the dielectric liner 131 frames the TSVs and protects against escape of the TSV filler (or core) material 113 into the semiconductor in the case of highly mobile metal TSV filler materials, such as Cu. For example, in one particular embodiment a 0.0875 µm Ta/TaN diffusion barrier metal layer then a 1.5 µm Cu seed layer 233 (see FIG. 2C) is deposited on the dielectric liner 131 for copper TSV filler material 113 embodiments. Alternatively, the seed layer 233 can, for example, comprise copper over titanium.

Figure 2C:
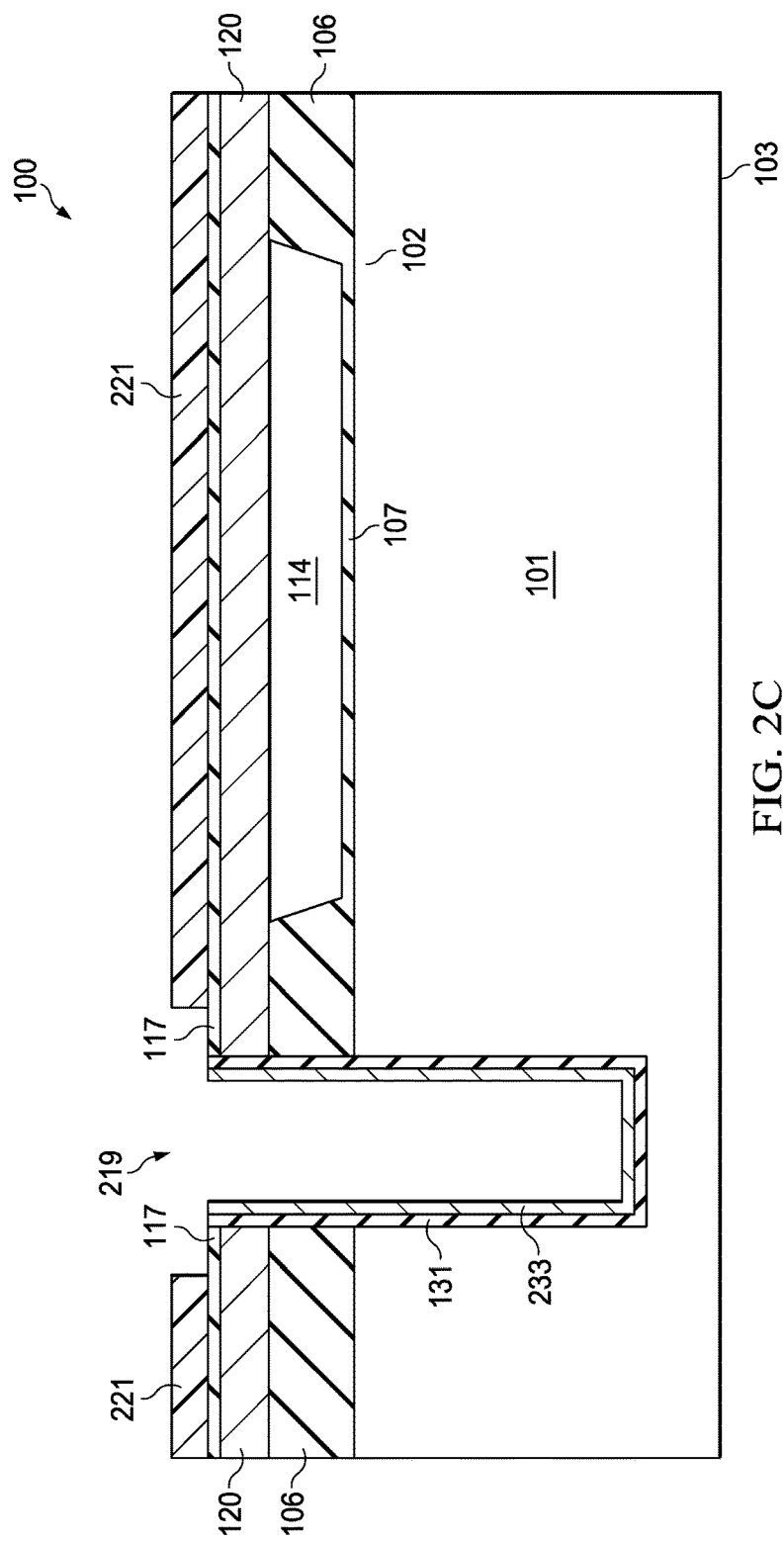

FIG. 2C shows a cross sectional depiction of the CMUT device in-process after the masking level Mask "CUMOLD" (Mask #3) which uses resist 221. This mask can be used to exclude a metal such as Cu from plating over portions of the CMUT cell. Negative resist can be used to ensure the TSV is resist free after masking. The mask is useful since the movable membrane 120b (e.g., a Si plate) may be deflected by several microns and the subsequent Cu chemical mechanical polishing (CMP) step in the case of copper filled TSVs may not fully remove the copper over the CMUT cells.

Figure 2D:
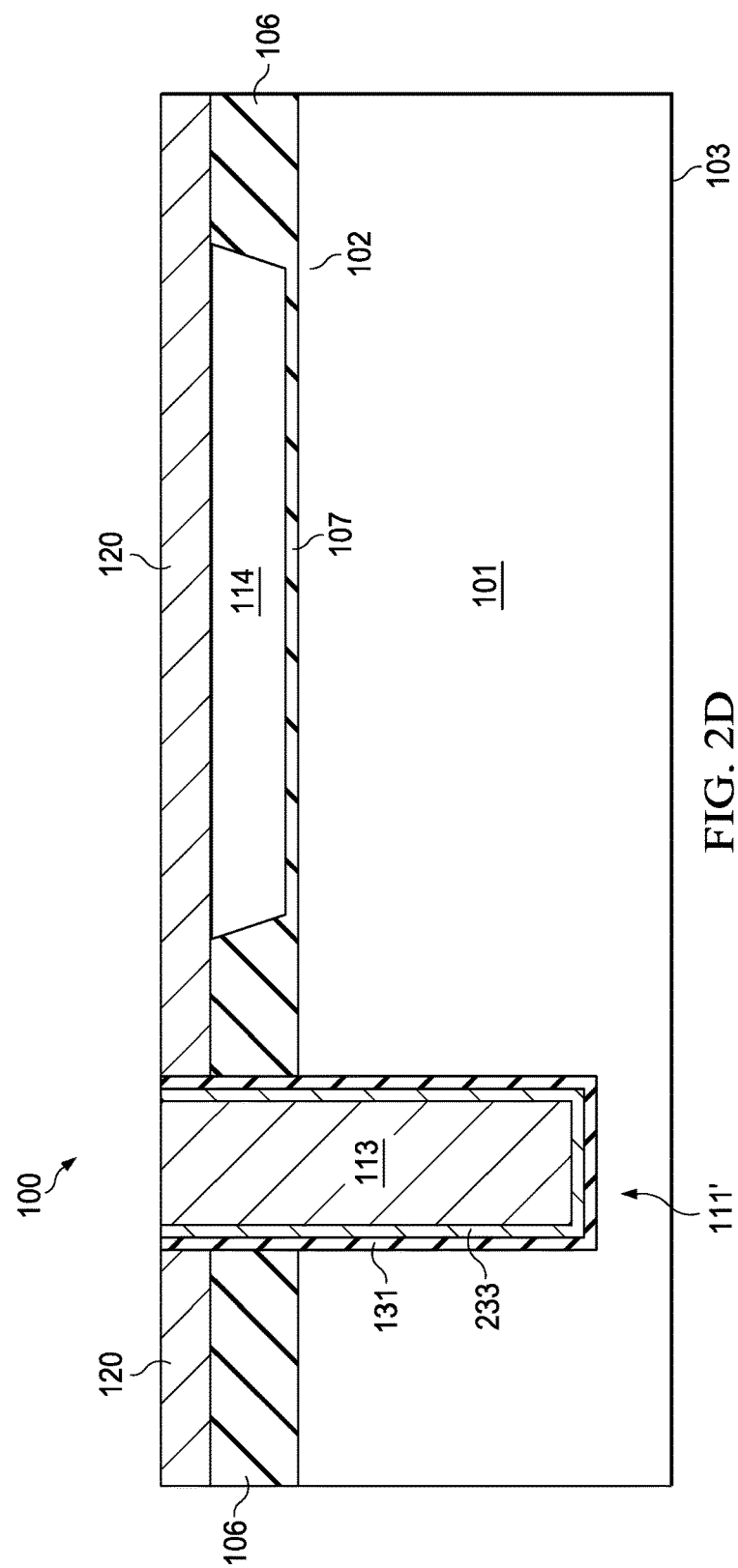

A metal layer is then deposited, such as electroplating a TSV filler material 113, (e.g., about 15 μm of Cu used) with a subsequent CMP to define the filled TSV hole 219 with the TSV filler material 113. The resist 221 is then stripped. FIG. 2D shows a cross sectional depiction of the CMUT device in-process after TSV filler material 113 deposition (e.g., Cu), CMP of the TSV filler material 113, where as shown the metal nail heads from the TSV filler material 113 on the seed layer 233 over and lateral to the embedded TSV 111' have been removed, and after dielectric liner 131 along with the buried dielectric layer 117 removal over the field area. An anneal step can follow. A second TSV CMP can be used to remove all remaining barrier metal if present (e.g. Cu+TaN). A wet strip may be used to clear residue over the CMUT cell. The dielectric liner 131 along with the buried dielectric layer 117 is then removed stopping on the membrane layer 120 (e.g., Si).

Figure 2E:
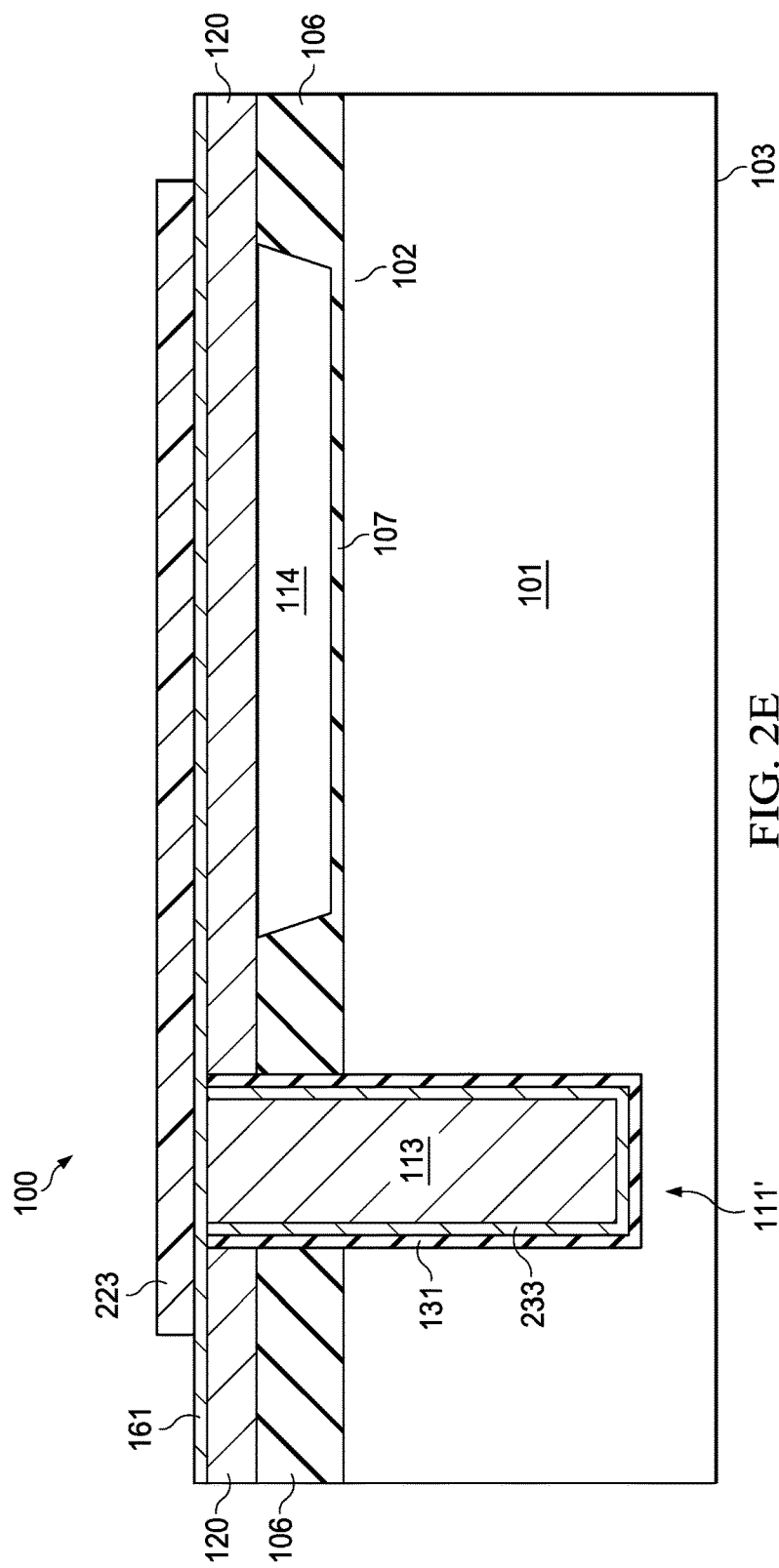
Figure 2F:
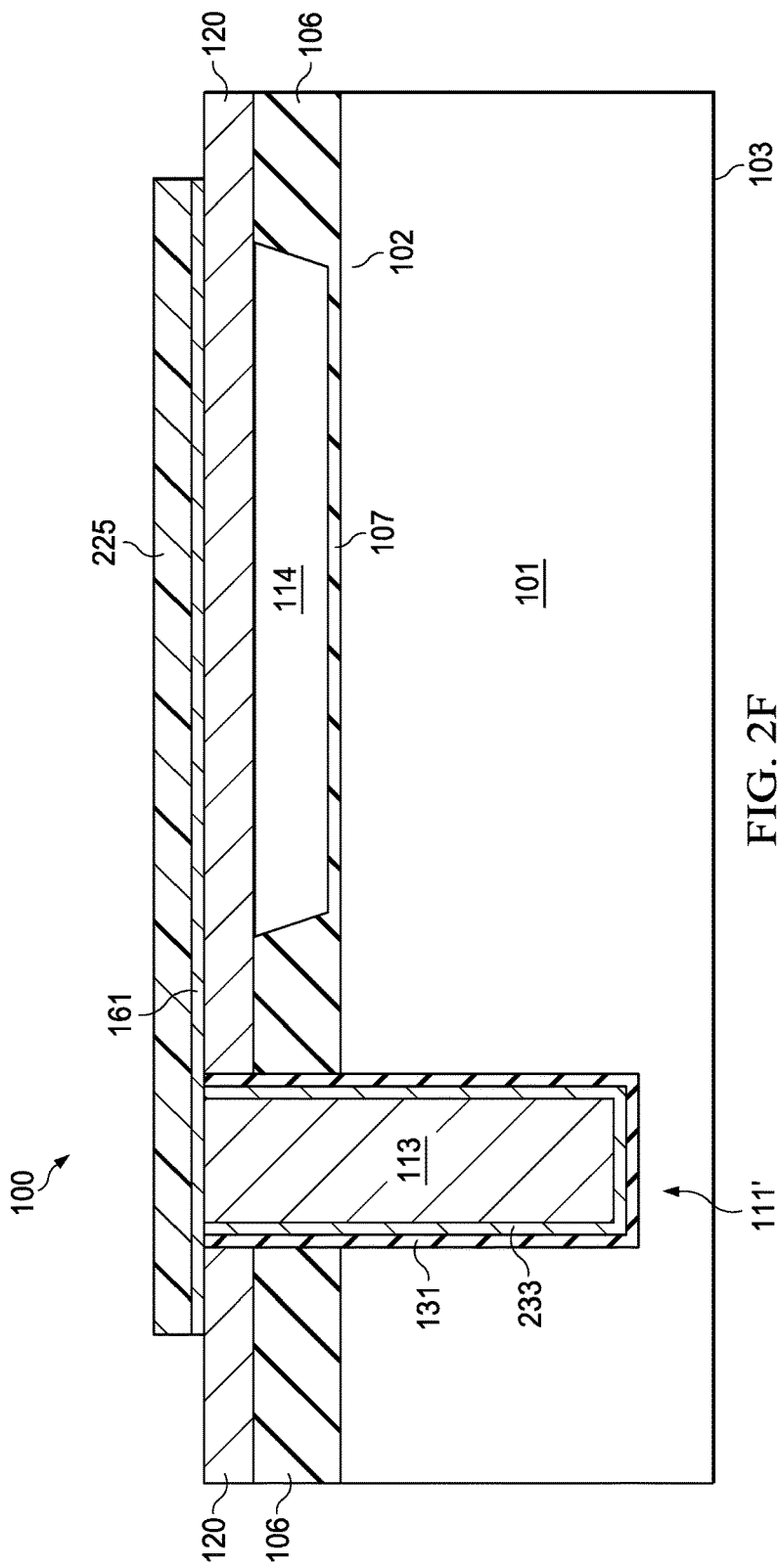

FIG. 2E shows a cross sectional depiction of the CMUT device in-process after deposition of a top side metal layer 161, such as 0.5 μm thick AlCu metal layer. Top side metal layer 161 provides the membrane layer 120 plate metallization and connects the membrane layer 120 to the top side of the embedded TSV 111'. The masking level ALTOP" (Mask #4) that uses resist 223 is shown which allows etching to define the top side metal layer 161 (e.g., AlCu layer) over the CMUT element(s). The ALTOP CDs can be smaller (e.g., 1 μm/side smaller) than the final to plate dimension. Patterning the top side metal layer 161 before patterning the movable membrane 120 (e.g., Si plate) avoids both top side metal layer 161 and resist step coverage issues. The top side metal layer 161 can be wet etched from the field area using the openings in the resist 223. The resist 223 is then stripped off FIG. 2F shows a cross sectional depiction of the CMUT device in-process after patterning of resist 225 using mask level "PLATESI" (Mask #5). The resist 225 can completely encapsulate the patterned top side metal layer 161 (e.g., AlCu layer). This mask can be larger (e.g., 1 μm/side larger) than the AlCu (ALTOP) mask described above.

The membrane layer 120 is then etched using resist 225 to separate the CMUT elements for CMUT devices having a plurality of CMUT elements and form the movable membrane 120b shown. The etch of the membrane layer 120 stops on the thick dielectric regions 106. A Bosch etch with a short cycle can be used to minimize side wall scalloping. The etch should be configured to not be reentrant. The resist 225 can then be stripped off.

Figure 2G:
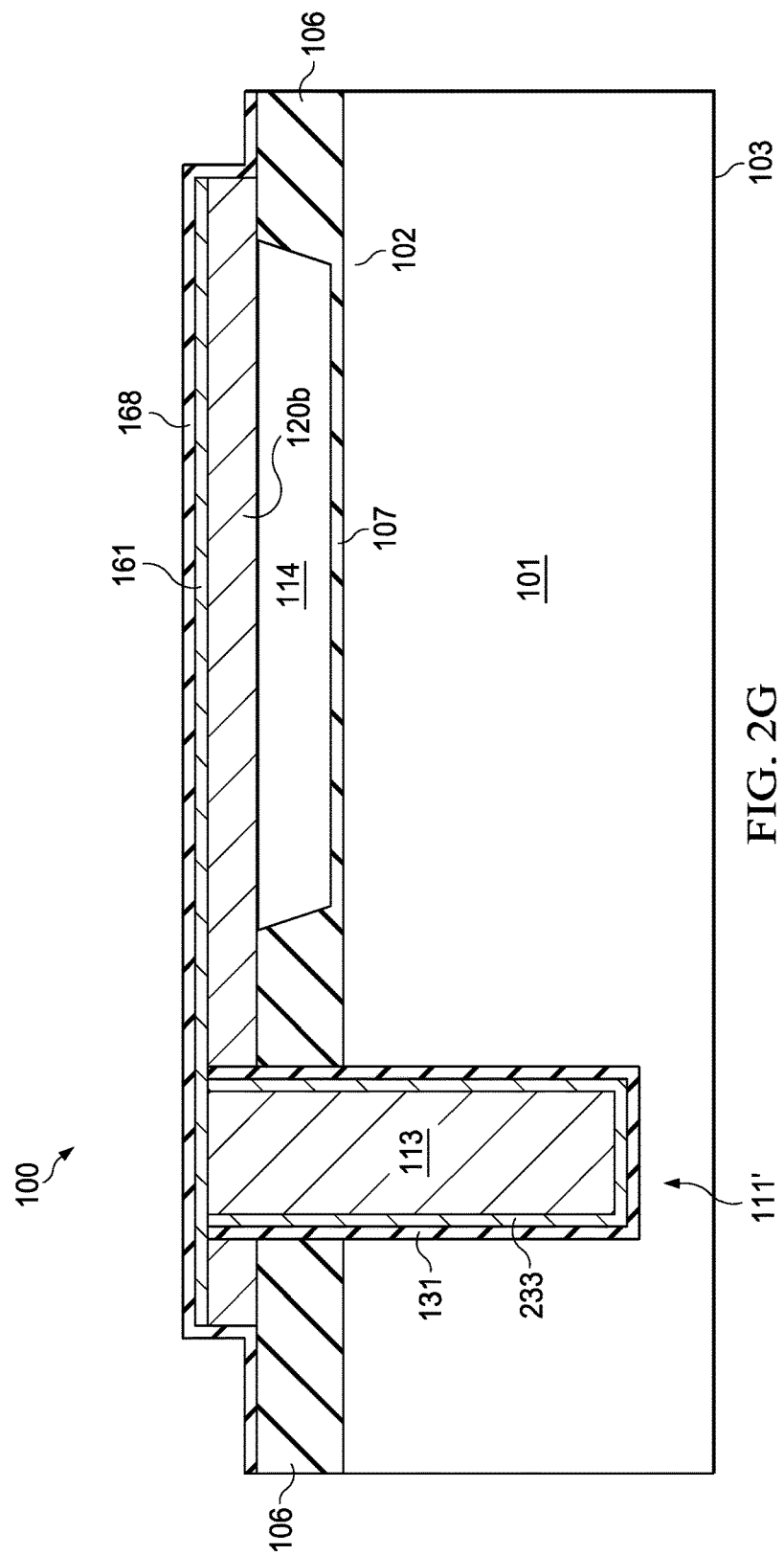

FIG. 2G shows a cross sectional depiction of the CMUT device in-process after depositing a dielectric passivation layer 168, such as about a 0.2 μm plasma tetraethyl orthosilicate (TEOS) derived silicon oxide layer, then a 0.2 μm plasma nitride passivation layer, in one particular embodiment. The dielectric passivation layer 168 is shown covering the sidewalls of the movable membrane 120b. Depending on the CMUT application a thicker passivation stack can be used. A final alloy can be performed, such as at 400° C. in $N_2+H_2$ (forming gas).

Figure 2H:
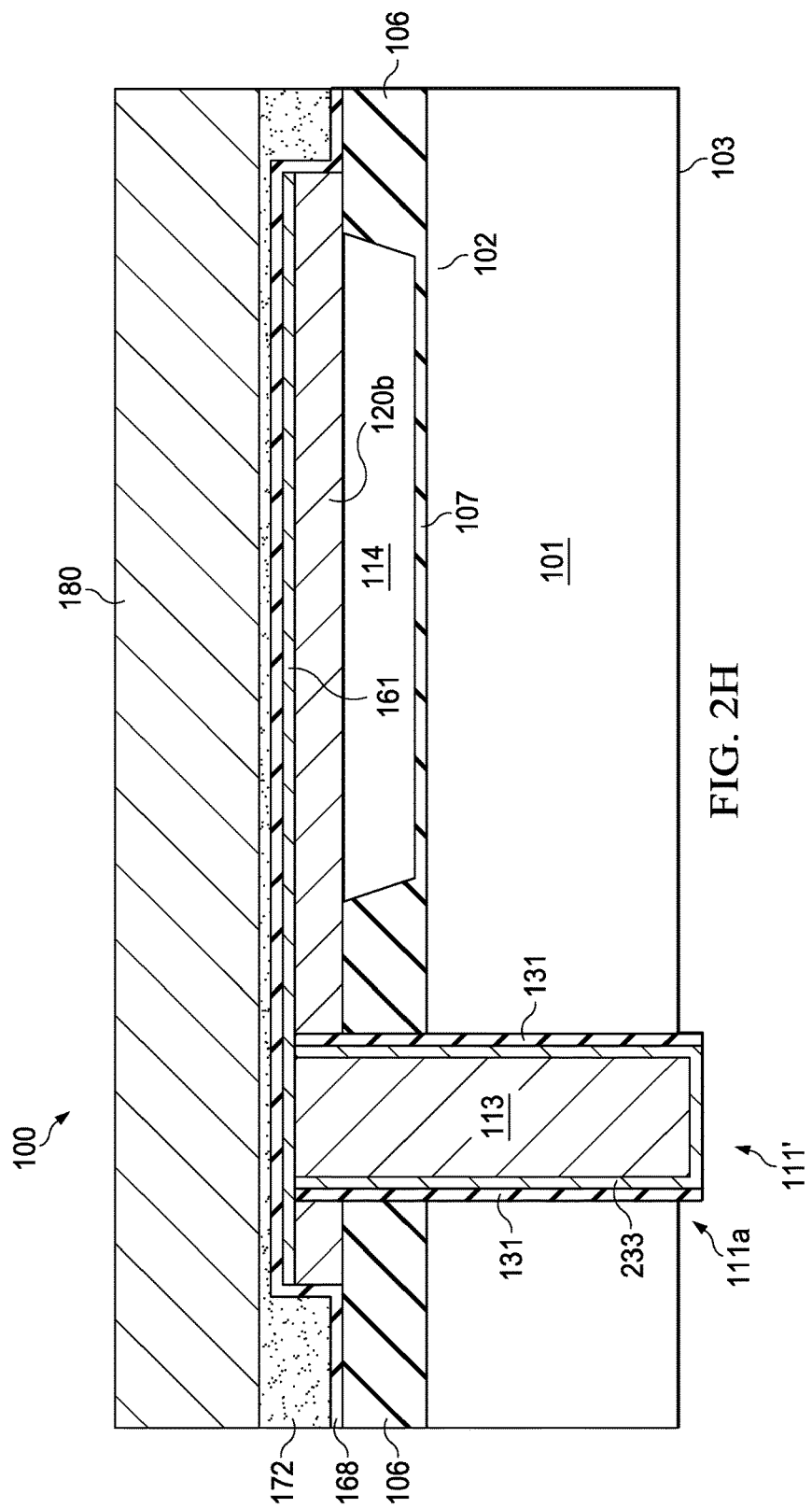

FIG. 2H shows a cross sectional depiction of the CMUT device in-process after optionally bonding the in-process CMUT substrate (e.g., wafer) to a temporary carrier wafer 180 using an adhesive 172, backgrinding then exposing the TSV on the bottom side 103 of the first substrate 101, and forming protruding TSV tips 111a. The backgrind can thin the in-process CMUT substrate (e.g., wafer) close to the embedded TSV, and can remove all bottom side films, and in one particular embodiment about 550 μm of a 725 μm thick Si substrate for first substrate 101 leaving about 175 μm. The bottom side 103 of the first substrate 101 can be etched to expose the TSV tips 111a leaving first substrate 101 to be about 100 μm thick. One can utilize a XeF plasma etch or wet Si etch, so that the dielectric liner 131 and the barrier metal (if present) are removed to form a TSV tip 111a having exposed TSV filler material 113 for the TSV 111. A plasma etch of the dielectric liner 131 and barrier metal will generally leave dielectric (e.g., oxide) spacers on the sidewalls of the TSVs 111 and 112.

A metal layer is then deposited on the bottom side 103 of the first substrate, such as a Ti/Ni/Ag layer in one specific embodiment (e.g., 1000Å Ti+2800Å Ni+1500Å Ag). The bottom side 103 of first substrate 101 can be cleaned before the metal layer 167 deposition. A pre-sputter etch of about 300 Å may be used. A masking level TSVEXP" (mask #6) can then be used to protect areas of the metal layer 167 while it is stripped from the TSV tip 111a. The CMUT device 100 shown in FIG. 1B described above results (the Cu seed layer 233 not shown in FIG. 1B) after patterning to form a patterned metal layer 167 on the bottom side 103 of first substrate 101, and stripping of the mask 6 resist. Following dicing (singulation), the resulting CMUT die can be packaged, such as bonded on top of a control die.

Figure 3:
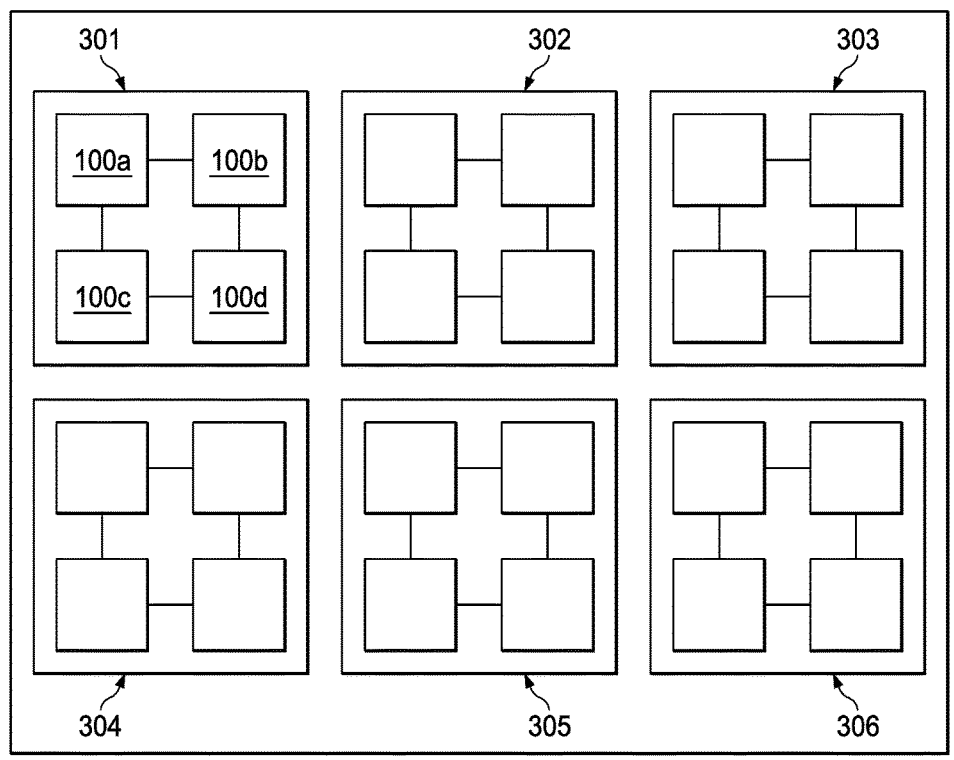
FIG. 3 is a top view depiction an example CMUT device including a plurality of CMUT elements each including a plurality CMUT cells shown in FIGS. 1A and 1B, according to an example embodiment.

FIG. 3 is a top view depiction an example CMUT device (die) 300 including a plurality of CMUT elements 301-306, with each capacitive CMUT element including four of the CMUT cells 100a in FIGS. 1A and 1B shown as CMUT cells 100a-100d connected together within the element, according to an example embodiment. As described above, the top electrodes can be separate for each CMUT element allowing separate addressing of the respective elements using a single TSV for each element, where there is common bottom side electrode (e.g., a solid sheet of Si) for all CMUT elements on the device. In other embodiments, the CMUT device has a common top electrode for each element and an individual bottom electrode for each element to allow separate addressing of the respective elements.

Although the CMUT device 300 is shown having six CMUT elements 301-306 with each CMUT element including four CMUT cells 100a-100d, disclosed CMUT devices can have any number of CMUT elements, each having any number of CMUT cells. The CMUT elements 301-306 can be electrically isolated from one another, connected in parallel on the die or off the die (e.g., by connecting their respective TSVs 111 to a common source) to reduce the impedance (for driving), or can be connected in series (on or off the die) to increase the impedance (for sensing). The respective CMUT elements can be driven/sensed differentially to improve common mode signals or mitigate manufacturing asymmetries.

Advantages of disclosed CMUT devices include the full process using as few as 4 mask levels. Other advantages include enabling smaller die size without the need for conventional bond pads which increase die size and require wire bonding to the couple to the ultrasonic transmitting surface (movable membrane 120b) on the top side of the CMUT device. Disclosed CMUT devices also simplify the packaging operation resulting in easy coupling to the transmitting medium, which reduces the packaging cost. Disclosed CMUT devices also facilitate the option of stacking the CMUT die on a control die since both electrodes are contacted from the bottom side of the CMUT device.

Disclosed embodiments can be used to form semiconductor die that may integrated into a variety of assembly flows to form a variety of different devices and related products. Those skilled in the art to which this disclosure relates will appreciate that many other embodiments and variations of embodiments are possible within the scope of the claimed invention, and further additions, deletions, substitutions and modifications may be made to the described embodiments without departing from the scope of this disclosure.

What is claimed is:

1. A transducer device, comprising:
a substrate having a first side and a second side opposite the first side;
a transducer cell, including:
a dielectric layer over the first side of the substrate, the dielectric layer having a first region and a second region thinner than and laterally surrounded by the first region to define a cavity;
a membrane layer enclosing the cavity and including a movable membrane over the second region of the dielectric layer; and
a through-substrate via (TSV) penetrating the substrate, the dielectric layer, and the membrane layer.

2. The transducer device of claim 1, wherein the membrane layer is bonded directly on the first region of the dielectric layer.

3. The transducer device of claim 1, wherein the TSV includes a conductive filler extending from the second side of the substrate to be coplanar with the membrane layer.

4. The transducer device of claim 1, further comprising:
a metal layer contacting the TSV adjacent to the first side of the substrate, the metal layer extending laterally along the membrane layer and contacting the movable membrane.

5. The transducer device of claim 1, wherein the membrane layer includes a single crystal silicon material.

6. The transducer device of claim 1, wherein the substrate has a resistivity less than or equal to 0.10 Ω-cm.

7. The transducer device of claim 1, further comprising:
a second transducer cell;
a metal layer connecting the second transducer cell to the TSV of the transducer cell adjacent to the second side of the substrate.

8. A transducer device, comprising:
a substrate having a first side and a second side opposite the first side;
a transducer cell, including:
a dielectric layer over the first side of the substrate, the dielectric layer having a first region and a second region thinner than and laterally surrounded by the first region to define a cavity;
a membrane layer enclosing the cavity and including a movable membrane over the second region of the dielectric layer;
a through-substrate via (TSV) penetrating the substrate, the dielectric layer, and the membrane layer, the TSV including a conductive filler and positioned laterally away from the movable membrane; and
a metal layer contacting the conductive filler above the first side of the substrate and extending laterally along the membrane layer to contact the movable membrane.

9. The transducer device of claim 8, wherein the membrane layer is bonded directly on the first region of the dielectric layer.

10. The transducer device of claim 8, wherein the membrane layer includes a single crystal silicon material.

11. The transducer device of claim 8, wherein the substrate has a resistivity less than or equal to 0.10 Ω-cm.

12. The transducer device of claim 8, further comprising:
a second transducer cell;
a second metal layer connecting the second transducer cell to the TSV of the transducer cell adjacent to the second side of the substrate.

13. A transducer device, comprising:
a substrate having a first side and a second side opposite the first side;
transducer cells, each including:
a dielectric layer over the first side of the substrate, the dielectric layer having a first region and a second region thinner than and laterally surrounded by the first region to define a cavity;
a membrane layer enclosing the cavity and including a movable membrane over the second region of the dielectric layer; and
a through-substrate via (TSV) penetrating the substrate, the dielectric layer, and the membrane layer, the TSV including a conductive filler; and
an interconnect metal layer connecting the conductive fillers of at least two of the transducer cells adjacent to the second side of the substrate.

14. The transducer device of claim 13, wherein the membrane layer is bonded directly on the first region of the dielectric layer.

15. The transducer device of claim 13, wherein the conductive filler extending from the second side of the substrate to be coplanar with the membrane layer.

16. The transducer device of claim 13, further comprising:
an intra-cell metal layer contacting the TSV adjacent to the first side of the substrate, the intra-cell metal layer extending laterally along the membrane layer and contacting the movable membrane.

17. The transducer device of claim 13, wherein the membrane layer includes a single crystal silicon material.

18. The transducer device of claim 13, wherein the substrate has a resistivity less than or equal to 0.10 Ω-cm.

* * * * *